(12) United States Patent
Langeveld et al.

(10) Patent No.: US 7,824,882 B2
(45) Date of Patent: Nov. 2, 2010

(54) OLIGOSACCHARIDES IN A TEST SYSTEM FOR THE DETERMINATION OF THE PRESENCE OF AN ANTIBIOTIC IN A FLUID

(75) Inventors: Pieter Cornelis Langeveld, Delft (NL); Johannes Theodorus Arie van Pelt, Delft (NL); Jacobus Stark, Rotterdam (NL); Tim de Graaf, Zoetermeer (NL)

(73) Assignee: DSM IP Assets B.V., Herleen (NL)

( * ) Notice: Subject to any disclaimer, the term of this patent is extended or adjusted under 35 U.S.C. 154(b) by 0 days.

(21) Appl. No.: 11/597,838

(22) PCT Filed: Jun. 2, 2005

(86) PCT No.: PCT/EP2005/052528

§ 371 (c)(1),
(2), (4) Date: Jan. 3, 2007

(87) PCT Pub. No.: WO2005/118837

PCT Pub. Date: Dec. 15, 2005

(65) Prior Publication Data

US 2008/0020420 A1   Jan. 24, 2008

(30) Foreign Application Priority Data

Jun. 2, 2004   (EP)   ................... 04076616

(51) Int. Cl.
*C12Q 1/18*   (2006.01)
*C12Q 1/02*   (2006.01)
*C12N 1/20*   (2006.01)

(52) U.S. Cl. ................... 435/32; 435/252.5; 435/253.4; 435/29

(58) Field of Classification Search ........................ None
See application file for complete search history.

(56) References Cited

U.S. PATENT DOCUMENTS

| 3,890,200 | A | * | 6/1975 | Jordan et al. ................... 435/36 |
| 5,354,663 | A | | 10/1994 | Charm et al. |
| 5,876,982 | A | | 3/1999 | Paul et al. |
| 6,867,015 | B1 | | 3/2005 | Langeveld et al. |
| 7,462,464 | B1 | | 12/2008 | Langeveld et al. |
| 2003/0068777 | A1 | | 4/2003 | Nakano et al. |
| 2006/0134725 | A1 | | 6/2006 | Langeveld et al. |
| 2007/0092929 | A1 | | 4/2007 | Dekker et al. |

FOREIGN PATENT DOCUMENTS

| EP | 0 285 792 A1 | 10/1988 |
| EP | 0 418 113 A2 | 3/1991 |
| EP | 0 832 984 A1 | 4/1998 |
| WO | WO 01/25795 A2 | 4/2001 |

OTHER PUBLICATIONS

International Search Report mailed Nov. 11, 2005 in PCT/EP2005/052528.
Written Opinion mailed Nov. 11, 2005 in PCT/EP2005/052528.

* cited by examiner

*Primary Examiner*—Lisa J Hobbs
(74) *Attorney, Agent, or Firm*—Nixon & Vanderhye P.C.

(57) ABSTRACT

Provided is a test system, a test method and a test kit for the determination of the presence of an antibiotic in a fluid based on a test medium comprising a test organism, at least one substance that provides a solid state, nutrients and an indicator, wherein the end-pH of said test medium at or after the time required for said determination is equal to or higher than 7.2 Said pH value can be realized by adding oligosaccharides, preferably a disaccharide or trisaccharide (eg. Lactose, gentobiose, maltotriose). Most preferably, said oligosaccharide is a non-reducing oligosaccharide (eg. Raffinose, sucrose or trehalose).

14 Claims, 1 Drawing Sheet

Figure 1:
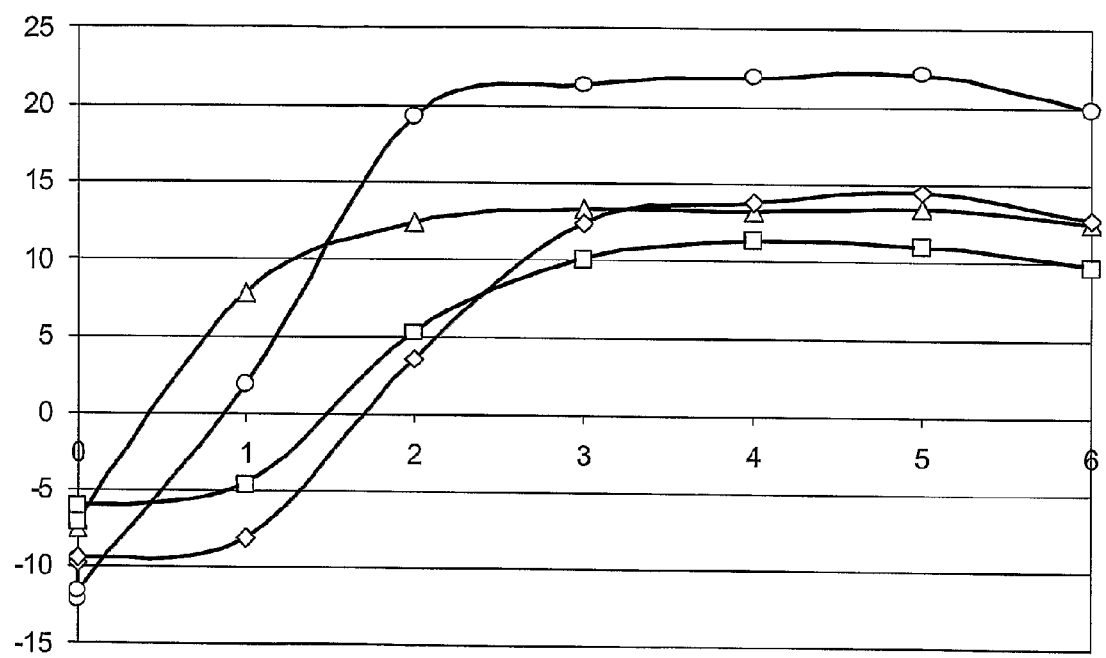

OLIGOSACCHARIDES IN A TEST SYSTEM FOR THE DETERMINATION OF THE PRESENCE OF AN ANTIBIOTIC IN A FLUID

This application is the US national phase of international application PCT/EP2005/052528 filed 2 Jun. 2005 which designated the U.S. and claims benefit of EP 04076616.4, dated 2 Jun. 2004, the entire content of which is hereby incorporated by reference.

FIELD OF THE INVENTION

The present invention relates to an improved novel microbiological test system and a new method for the rapid determination of the presence of antibacterial compounds in fluids such as milk, meat juice, serum and urine using said test system.

BACKGROUND OF THE INVENTION

Microbiological test methods for the determination of antibacterial compounds, particularly residues of antibiotics such as cephalosporin, penicillin, tetracycline and derivatives thereof and chemotherapeutics such as sulfa's, in fluids such as milk, meat juice, serum and urine have been known for a long time. Examples of such tests have been described in CA 2056581, DE 3613794, EP 0005891, EP 0285792, EP 0611001, GB A 1467439 and U.S. Pat. No. 4,946,777. These descriptions all deal with ready to use tests that make use of a test organism and will give a result by the change indicated by an indicator molecule added to the test system. The principle is that when an antibacterial compound is present in the fluid in a concentration sufficient to inhibit the growth of the test organism the color of the indicator will stay the same, while, when no inhibition occurs, the growth of the test organism is accompanied by the formation of acid or reduced metabolites or other phenomena that will induce an indicator signal.

The test systems mentioned above include a test medium, such as an agar medium, inoculated with a test organism, preferably a strain of *Bacillus*, *Escherichia coli* or *Streptococcus*, and a pH indicator and/or a redox indicator. The test organism and the indicator are introduced into an optionally buffered agar solution wherein nutrients are present and optionally substances to change the sensitivity to certain antimicrobial compounds. The agar solution is allowed to solidify to form the test medium such that the test organisms stay alive but cannot multiply because of low temperature. A suitable test should have the desired sensitivity with regard to the compounds to be tested for.

The test systems currently distributed on the market and/or described in literature all have a certain range in which indicator color changes occur. The width of this range determines how accurate a given test system performs. Many of the known test systems display different results when tests are read after a predetermined amount of time or after the time required for a blank sample to change color. It is desirable to develop test systems whereby the range in which the indicator color change occurs is smaller and/or more easily readable and/or having an improved sensitivity than in known systems whilst simultaneously the stability of the test organism is warranted and whereby there are smaller differences between tests that are determined after a predetermined amount of time versus tests that are determined at the moment that a blank sample changes color.

SUMMARY OF THE INVENTION

It is an object of the present invention to provide an improved test system and method for the determination of antibiotics in fluids. Surprisingly, we have found that there is a positive effect attainable when using a test system having a high pH value at or after the time required for said determination.

Said high pH value can be realized by adding certain components, such as oligosaccharides such as a disaccharide and/or a trisaccharide as one of the components of the test system. It has been found that the use of a disaccharide and/or a trisaccharide results in a test system showing an increased pH-value with respect to comparable systems without di- and/or a trisaccharide. Furthermore, by applying oligosaccharides such as a disaccharide and/or a trisaccharide according to the present invention in microbiological test systems, an advantage in indicator color change as a function of antibiotics concentration can be achieved. Additionally, it has been found that the use of a disaccharide and/or a trisaccharide results in a test system showing an improved stability with regard to the test organism used.

The present invention provides a test system for the determination of the presence or absence of an antibiotic in a fluid comprising a test medium comprising a test organism, at least one substance that provides a solid state, nutrients and an indicator, characterized in that the end-pH of said test medium at or after the time required for said determination is equal to or higher than 7.2.

Furthermore, there is provided a method for the determination of the presence or absence of an antibiotic in a fluid comprising the steps of:

(a) contacting a sample of said fluid with a test medium comprising a test organism, at least one substance that provides a solid state and an indicator;

(b) incubating the test organism for a period of time to grow the test organism in case no antibiotic is present in the fluid sample; and (c) detecting growth or inhibition of growth of the test organism with the indicator, characterized in that said test system is a test system for the determination of the presence of an antibiotic in a fluid comprising a test medium comprising a test organism, at least one substance that provides a solid state, nutrients and an indicator suitable for the detection of penicillin G, characterized in that the end-pH of said test medium at or after the time required for said determination is equal to or higher than 7.2.

Additionally, the present invention provides a kit suitable for the determination of the presence or absence of an antibiotic in a fluid comprising:

(a) at least one container partially filled with a test medium comprising a test organism, at least one substance that provides a solid state, nutrients and an indicator, and;

(b) a device for adding fluid to the test medium, characterized in that the end-pH of said test medium at or after the time required for said determination is equal to or higher than 7.2.

Finally there is provided the use of an oligosaccharide as nutrient in a test system for an antibiotic.

DETAILED DESCRIPTION OF THE INVENTION

The terms and abbreviations given below are used throughout this disclosure and are defined as follows.

The term 'CFU' is an abbreviation of Colony Forming Units and refers to the number of organisms, spores of organisms, partially germinated spores of organisms or vegetative cells capable of producing colonies of organisms.

The term 'end-pH' refers to the pH-value of a test system comprising an indicator measured on or after a certain moment. This moment is defined as the moment in time at which the indicator, in a test system when used upon a sample that should generate a change in the status of the indicator, actually displays a significant change in said status.

The term 'fluid' refers to a substance (as a liquid, not a gas) tending to flow or conform to the outline of its container.

The term 'gelling agent' refers to a compound that assists in changing a mixture into or taking on the form of a gel.

The term 'indicator' refers to a substance used to measure (for example by change of color or fluorescence) the condition of a test medium with respect to the presence of a particular material (for example an acid, a base, oxidizing or reducing agents). For instance, the term 'indicator' may refer to one or more compounds that are known as pH-indicators, but also to one or more compounds that are known as redox-indicators. Also, the term 'indicator' may refer to mixtures of two or more different types of indicators, such as a combination of a pH- and a redox-indicator. In general, when two or more indicators are used, these indicators are co-operating to increase the indicator effect of each of the indicators when taken alone.

The term 'non-reducing oligosaccharide' refers to an oligosaccharide lacking an anomeric hydroxyl group, or in other words, lacking a free anomeric carbon atom. Examples of non-reducing oligosaccharides are the well known naturally occurring raffinose, sucrose and trehalose, but also less known and/or synthetically prepared non-reducing oligosaccharides are meant to be included in the scope of this definition.

The term 'nutrient' refers to one or more nutritive substances or ingredients that promote and/or are required for the growth of test organisms as used in the method of the present invention.

The term 'oligosaccharide' refers to at least two monosaccharides that are covalently linked. The person skilled in the art is aware that the upper range of the term oligosaccharide is not well defined in literature. However in the present invention the term oligosaccharide may include up to 20 to 50 monosaccharides, or even up to 100 or 150 monosaccharides as long as there is solubility in aqueous solution of at least 1 mg·l$^{-1}$.

The term 'sensitivity' refers to the degree of receptiveness of a given system to sense a certain state. More particularly, in the present case 'sensitivity' refers to the degree by which concentrations of antibiotics in a sample can be determined.

The term 'spore' refers to a primitive usually unicellular often environmentally resistant dormant or reproductive body produced by organisms and capable of development into a new individual organism.

The term 'test medium' refers to a composition such as a solution, a solid or, preferably, in the form of a sol or a gel, for instance comprising a gelling agent. Suitable examples of gelling agents are agar, alginic acid and salts thereof, carrageenan, gelatin, hydroxypropylguar and derivatives thereof, locust bean gum (Carob gum), processed eucheuma seaweed and the like. However, the person skilled in the art will understand that other types of solid test media may be based on carrier materials such as ceramics, cotton, glass, metal particles, paper, polymers in any shape or form, silicates, sponges, wool and the like. Usually, a test medium contains one or more indicators, however, these compounds may also be added later when the test is being performed. The test medium comprises one or more types of test organisms as detecting agents and nutrients. Optionally, the test medium may also contain one or more buffers, stabilizers, substances that change the sensitivity to certain antimicrobial compounds in a positive or negative way, and/or viscosity-increasing agents. When a buffer is present in the medium, it may be added during the mixing of the components of the medium or the components may be dissolved and/or suspended in the buffer. Optionally the test medium is sterilized and usually the pH is adjusted to the required value. Examples of substances that change the sensitivity to certain antimicrobial compounds are antifolates like ormethoprim, tetroxoprim and trimethoprim that improve the sensitivity of the test organism towards sulfa compounds or salts of oxalic acid or hydrofluoric acid, which improve the sensitivity towards tetracycline. Examples of viscosity-increasing agents are ascorbyl methylsilanol pectinate, carbomer, carboxymethyl cellulose, cetearyl alcohol, cetyl alcohol, cetyl esters, cocamide DEA, emulsifying wax, glucose, hydroxyethyl cellulose, hydroxypropylmethyl cellulose, lauramide DEA, linoleamide DEA, magnesium aluminum silicate, maltodextrins, PEG-8 distearate, polyacrylamide, polyvinyl alcohol, PVP/hexadecene copolymer, sodium chloride, sodium sulfate, soyamidopropyl betaine, xanthan gum and the like. Alternatively, the optional ingredients of the test medium mentioned above may also be added exogenously. The test medium may be contained within any type of container; frequently used containers are tubes, microtiter plates and petri dishes.

The term 'threshold' refers to the concentration value above which a given analyte is to be regarded as present and below which said analyte is to be regarded as absent. Generally, a threshold value is given for particular analytes in particular samples by local, regional or interregional authorities but it can also be pre-set for certain research purposes.

In a first aspect of the invention there is provided a test system that comprises a test medium. The test medium comprises a test organism, nutrients, a substance that provides a solid state and at least one indicator. The end-pH of said test medium at or after the time required for said determination is equal to or higher than 7.2. Typical end-pH values of the test systems of the present invention are values exceeding 7.3, and they are preferably between pH 7.5 and pH 9, more preferably between pH 7.8 and pH 8.5, most preferably between pH 7.9 and pH 8.3. Test systems with the above pH characteristics have the advantage that the color of the indicator displays an increased intensity. This intensity increase greatly facilities interpretation and leads to higher degree of accuracy and an improved sensitivity towards one, some or all of the components that are to be detected by the test system. Surprisingly, at these increased pH-values, the sensitivity towards β-lactam antibiotics either remains the same or improves and the sensitivity towards tetracycline remains unchanged. Both types of compounds are however well known for their instability in alkaline environment.

The way by which the above pH values, which are higher than those known from prior art test systems, are realized is in principle not important. Addition of any component that will lead to the required pH values suffices. Preferred components are those that do not otherwise disturb the functioning of the test system. Examples of classes of compounds suitable for this purpose are bases, buffers, nutrients, oligosaccharides, peptides, salts and yeast extracts. The way by which the pH values are measured is important as differences in measured pH values may occur as a function of differences in measuring conditions. To this end, the pH values of prior art test systems and of the test systems of the present invention are established following the detailed procedure as outlined in Example 1.

In one embodiment, it was established that the use of an oligosaccharide such as a disaccharide and/or a trisaccharide results in a test system showing an increased pH-value with respect to comparable systems without such an oligosaccharide. In particular, this effect typically (also) occurs at the end of a test run, i.e. when the test organism has had the opportunity to grow (the so-called end-pH). In this embodiment, at least one component of the nutrients is an oligosaccharide. Preferably the oligosaccharide is partly soluble in aqueous solutions and preferably the oligosaccharide contains one or more glucose units. More preferably the oligosaccharide is a relatively short-chained oligosaccharide such as a disaccharide, a trisaccharide, a tetrasaccharide or a pentasaccharide. Suitable disaccharides are cellobiose, gentiobiose, lactose, maltose, sucrose or trehalose. Suitable trisaccharides are maltotriose, melezitose and raffinose. Most preferably the oligosaccharide is a non-reducing oligosaccharide as it was established that these compounds in particular have the additional advantage that in their presence the production of batches of test medium leads to an improved stability of the test microorganism. Suitable examples of non-reducing oligosaccharides are raffinose, sucrose and trehalose. Surprisingly, it was found that when using sucrose, not only the required pH-effect was obtained, but also the stability of the test system was not negatively affected. The oligosaccharide may be the only saccharide present in the test medium, but it may also be combined with other saccharides such as monosaccharides (i.e. glucose) and/or oligosaccharides. The amount of oligosaccharide in the test medium is between 0.1 and 500 $g \cdot l^{-1}$ test medium, preferably between 1 and 100 $g \cdot l^{-1}$, more preferably between 1.5 and 75 $g \cdot l^{-1}$, most preferably between 2 and 50 $g \cdot l^{-1}$. By applying oligosaccharides as described above, test systems are obtained that display a smaller range in which the indicator color change occurs, wherein the stability of the test organism is warranted and whereby there are smaller differences between tests that are determined after a predetermined amount of time versus tests that are determined at the moment that a blank sample changes color.

Other suitable nutrients that may be present next to the oligosaccharide are carbon-sources and nitrogen-sources of which many commercially available variants exist. Typical constituents are amino acids, monosaccharides, vitamins and the like.

The skilled artisan will appreciate that many indicators are suitable for the purpose of the present invention. Particularly useful are indicators that, upon changing from one state to the other, provide a visually detectable signal such as a change in color or fluorescence. The amount of indicator in the test medium is between 0.01 and 50 $g \cdot l^{-1}$ test medium, preferably between 0.1 and 10 $g \cdot l^{-1}$, more preferably between 0.5 and 5 $g \cdot l^{-1}$, most preferably between 1 and 3 $g \cdot l^{-1}$. Such indicators may be easily selected from handbooks such as 'H. J. Conn's Biological Stains', R. D. Lillie ed., Baltimore, 1969. Preferred indicators are pH-indicators and/or redox indicators. Examples of suitable indicators are Acid Blue 120, Acid Orange 51, Acid Yellow 38, Alizarin acid, Alizarin Blue, Azure A, Azure B, Basic Blue 3, Brilliant Black, Brilliant Cresyl Blue, Brilliant Crocein MOO, Brilliant Yellow, Bromocresol Green, Bromocresol Purple, Bromophenol Blue, Bromophenol Red, Bromothymol Blue, Chlorocresol Green, Congo Red, m-Cresol Purple, Gallocyanine, Indigo Carmine, Janus Green B, Litmus, Methylene Blue, Nile Blue A, Nitrazol Yellow (also referred to as Nitrazine Yellow), o-Nitrophenol, p-Nitrophenol, 1-10 Phenanthroline, Phenolphthalein, Safranine O, Thionin, Thymol Blue, Toluidine Blue and Xylenol Blue.

Preferably, the substance providing for a solid state is a gelling agent and/or a carrier material. The amount of gelling agent in the test medium is between 1 and 200 $g \cdot l^{-1}$ test medium, preferably between 2 and 50 $g \cdot l^{-1}$, more preferably between 5 and 20 $g \cdot l^{-1}$, most preferably between 7 and 15 $g \cdot l^{-1}$. Preferred gelling agents are agar and gelatin.

In another embodiment of the first aspect of the invention, the test organism is a thermophilic test organism such as a *Bacillus* species, preferably *Bacillus stearothermophilus*, an *Escherichia coli* species, or a *Streptococcus* species, preferably *Streptococcus thermophilus*. These species may be introduced in the test as units capable of producing colonies, or Colony Forming Units (CFU's). Said CFU's may be spores, vegetative cells or a mixture of both. The concentration of said CFU's is expressed as Colony Forming Units per ml of test medium (CFU·ml$^{-1}$) and is usually in the range of $1 \times 10^5$ to $1 \times 10^{12}$ CFU·ml$^{-1}$, preferably $1 \times 10^6$ to $1 \times 10^{10}$ CFU·ml$^{-1}$, more preferably $2 \times 10^6$ to $1 \times 10^9$ CFU·ml$^{-1}$, most preferably $5 \times 10^6$ to $1 \times 10^8$ CFU·ml$^{-1}$, or still more preferably $5 \times 10^6$ to $2 \times 10^7$ CFU·ml$^{-1}$.

In a second aspect of the invention, there is provided a method for the determination of an antibiotic in a fluid comprising the steps of contacting a sample of said fluid with a test medium according to the first aspect of the present invention. Advantageously, the method provides for conditions that there is no growth of test organism prior to the addition of fluid sample, by keeping the test medium at conditions that prevent growth, such as a relatively low temperature and/or by preparing the test medium immediately prior to use. After addition of the fluid sample, growth of the test organism is allowed to take place during a period sufficiently long for the test organisms to grow in case no antibiotics are present, by raising the temperature and/or providing for a pH-value at which the test organism is able to grow; and detecting growth of the test organism by observing the presence or absence of a change of an indicator. The method of the present invention also includes mixing samples (e.g. with other samples, but also with salts, buffering compounds, nutrients, stabilizers, isotope-labeled compounds, fluorescence-labeled compounds and the like), concentrating and/or diluting (e.g. with diluting liquids such as water, milk or liquids derived from milk, blood or liquids derived from blood, urine and/or solvents) samples prior to addition to the test medium.

In one embodiment of the second aspect of the present invention, the antibiotic is a β-lactam antibiotic such as a cephalosporin or a penicillin derivative. Examples of such derivatives are amoxicillin, ampicillin, cefadroxil, cefradine, ceftiofur, cephalexin, penicillin G, penicillin V and ticarcillin, but of course many other similar β-lactam derivatives are known and applicable in the method of the present invention. In another embodiment the antibiotic is an aminoglycoside such as, for instance, neomycin.

Advantageously, it was established that the method of the present invention displays a very narrow range in which the indicator changes color as a function of the concentration of antibiotics.

In another embodiment of the second aspect of the invention, the growth of the test organism is to take place during a predetermined period, preferably within a time span of 0.5 to 4 hours, more preferably between 1 to 3.5 hours, most preferably between 2.0 to 3.25 hours. Preferably the growth of the test organism is conducted at a predetermined temperature, preferably the optimal growth temperature of the test organism. When, for example, thermophilic test organisms are used, said temperature preferably is between 40 and 70° C., more preferably between 50 and 65° C., most preferably between 60 and 64° C. Optionally said reaction can be carried out with the aid of a thermostatic device. Alternatively, the time required for growth of the test organism is equal to the time that is required for a calibration sample without any analyte to induce a change in the indicator.

In still another embodiment of the second aspect of the invention, some of the nutrients are added as a separate source, e.g. as a tablet, disc or a paper filter. Also other compounds such as the indicator(s), test organism, stabilizers and/or antifolates may be added as a separate source, optionally incorporated in the nutrient medium.

In yet another embodiment of the second aspect of the invention, there is provided a method for determining the presence or absence of an antibiotic in a fluid sample whereby the ratio of the fluid sample to test medium exceeds 2:3 (0.68:1) (v/v). Preferably, said ratio is at least 20:27 (0.74:1) (v/v), more preferably said ratio is at least 25:27 (0.93:1) (v/v); most preferably said ratio is at least 2:1 (v/v). It has been found that there is no technical reason for an upper limit to the amount of fluid sample. In practice this volume should not exceed the maximum content of the container that holds the test medium. For example, in a 2 ml container having 0.2 ml test medium, no more than 1.8 ml of fluid sample should be added. In practice, containers for performing the method of the present invention have a volume that rarely exceeds 50 ml and hence the amount of fluid sample to be added shall not exceed 50 ml, preferably 10 ml, more preferably 5 ml, still more preferably 2 ml, most preferably 1 ml. Thus, in general, the upper limit of the ratio of the volume of fluid sample to the volume of test medium is 250:1 (v/v), preferably 50:1 (v/v), more preferably 25:1 (v/v), still more preferably 10:1 (v/v), most preferably 5:1 (v/v). Preferably, the volume of fluid sample is greater than the volume of test medium.

The result of the method of the present invention is determined by the observation of the presence or absence of a change of the indicator or indicators used. When, for example, such a change is a color change, said color change may be observed visually. However in one embodiment of the invention said color change is determined using an arrangement that generates digital image data or an arrangement that generates analog image data and converts said analog image data into digital image data followed by interpretation of said digital image data by a computer processor. Such an arrangement, which may for instance be a sample-reading device such as a scanner coupled to a personal computer, is described in International Patent Application WO 03/033728, incorporated by reference, and briefly summarized below.

The arrangement can be suitably used for instance for detecting residues of antibiotics in milk. With this arrangement it is possible to scan the bottom side of each of the samples in a test plate. The color and the brightness of the reflected light are registered in three variables, each describing one color component, for instance the so-called L*a*b* model. In the L*a*b* model, the color spectrum is divided in a two-dimensional matrix. The position of a color in this matrix is registered by means of the two variables "a" and "b". The variable L indicates the intensity (for instance, from light blue to dark-blue). It is possible to make a criterion comprising the a-value, b-value and L-value to make a composite function as follows:

$$Z = w_L \cdot L + w_a \cdot a + w_b \cdot b$$

where $w_L$, $w_a$ and $w_b$ are weighting factors for the L-value, a-value and b-value, respectively. The values of these weighting factors can be calculated by means of "discriminent analysis", such that the group means show a maximum distance in relation to the spreading. By combining two or more of the color components in the L*a*b* model in a predetermined manner that depends on the type of residue and the sample, an accurate detection is possible. In practice, a certain value of Z at which a test should switch between positive and negative result is experimentally predetermined.

In a third aspect of the invention there is provided a kit for carrying out the method of the second aspect of the present invention. Such a kit comprises one or more containers filled with test medium as described in the first aspect of the invention and optionally a sampling device. The containers may be test tubes of any shape and size and from any material available, provided that observation of indicator changes is possible. Also, the containers may be wells such as those incorporated in micro-titer plates.

Said sampling device is a device with the aid of which fluid can be added to said test medium. Preferably, such a device is a container, optionally with volume markings. More preferably, such a device is a syringe, a pipette or an automated pipetting system. Such a syringe or pipette may be designed in such a fashion that with only one mode of operation a predetermined volume can be withdrawn from the fluid to be analyzed. Optionally, systems known in the art with which more than one syringe or pipette can be operated with one single handling may be applied. It is the object of the third aspect of the present invention to provide a kit that allows for simple addition of the amounts of fluid to be added according to the second aspect of the invention. Optionally, said kit comprises means for sealing of said containers filled with test medium during incubation and/or an insert with instructions for use and/or a means for setting the time needed for incubation.

In another embodiment of the third aspect of the present invention, said kit comprises a thermostatic device, with the aid of which test samples can be kept at a pre-set temperature, such as the temperature at which the test organism shows sufficient growth. Preferably, said thermostatic device is designed in such a fashion that it can hold said containers filled with test medium. Optionally the thermostatic device is coupled to a means for setting the time needed for incubation such that heating and/or cooling is stopped after lapse of a pre-set period.

In yet another embodiment of the third aspect of the invention, said kit comprises a data carrier loaded with a computer program suitable for instructing a computer to analyze digital data obtained from a sample-reading device. Said data carrier may be any carrier suitable for storing digital information such as a CD-ROM, a diskette, a DVD, a memory stick, a magnetic tape or the like. Advantageously, said data carrier loaded with a computer program provides for easy access to the latest available computer programs suitable for use in the method of the present invention.

In a fourth aspect of the present invention there is provided the use of an oligosaccharide as nutrient in a test system for an antibiotic. Preferably said test system is a microbial inhibition test. Preferably said oligosaccharide is a disaccharide or a trisaccharide such as cellobiose, gentiobiose, lactose, maltose, maltotriose, melezitose, raffinose, sucrose or trehalose. Most preferably, said oligosaccharide is a non-reducing oligosaccharide such as raffinose, sucrose or trehalose.

LEGEND TO THE FIGURE

FIG. 1 shows the relationship between the concentration of penicillin G (x-axis, in ppb) and the Z-value (y-axis) in various test systems. As outlined in the detailed description, the following equation was used: $Z=0.35 \cdot a+0.65 \cdot b$. Color values were measured at the point in time where a sample without antibiotics (i.e. 0 ppb penicillin G) changes color from purple to yellow. The explanation of the symbols used in the Figure is as follows.

Δ: Copan test;
◇: DSM Delvotest® MCS test;
□: DSM Delvotest® SP test;
○: DSM Delvotest® MCS test with sucrose.

EXAMPLES

Example 1

Determination of the End-pH in a Test System

The pH-values as measured and mentioned in the present application were established as follows. A Radiometer PHM 82 standard pH-meter equipped with a PHC2005 pH-electrode was used at 20±3° C. The temperature setting on the pH-meter was set at 20° C. The pH-meter was calibrated with two commercial fresh buffer solutions, one of pH 4 and one of pH 7, according to the following procedure. The pH-electrode was rinsed with deionized water and inserted into the pH 7 buffer and after at least 10 seconds the value on the display was set, using the buffer regulator, at 7.0. The pH-electrode was rinsed with deionized water and inserted into the pH 4 buffer and after at least 10 seconds the value on the display was set, using the sense regulator, at 4.0. The pH-electrode was rinsed with deionized water and inserted into the pH 7 buffer and the value displayed was observed after at least 10 seconds; if this value was not within the range 6.95-7.05, the calibration procedure was repeated as often as was necessary to obtain a value within said range. The pH-values of the various test systems were determined as follows. The test system to be investigated was incubated until the end-pH as defined in the detailed description was reached. This was repeated with a series of identical incubations the number of which was sufficient to obtain, after pooling of the test media, a combined volume of test medium of 1.7-2.0 ml. Sample fluid was removed from each test system prior to pooling. Thus, for test systems comprising 250 μl of test medium (i.e. Delvotest® ampoules), 8 identical tests were pooled, whereas for test systems comprising 170 μl of test medium (i.e. Delvotest® plate tests), 10 identical tests were pooled The combined test media were allowed to reach a temperature of 20±3° C., followed by insertion of the pH-electrode (after it was rinsed with deionized water) into the combined test media and recording the pH-value as shown in the display after at least 10 seconds.

Example 2

End-pH Value of Several Commercially Available and Newly Developed Test Systems

Using the measuring method described in Example 1, the end-pH of several test systems was determined. The results are given in the Table below.

| | Test system | T (min) | pH value measured after time T |
|---|---|---|---|
| 1 | DSM Delvotest ® SP test | 150 | 6.79 |
| 2 | DSM Delvotest ® MCS test | 150 | 7.16 |
| 3 | Copan test (ampoule) | 150 | 7.03 |
| 4 | Copan test (plate) | 150 | 6.96 |
| 5 | AM test | 190 | 6.79 |
| 6 | DSM Delvotest ® MCS test with sucrose (ampoule) | 150 | 7.47 |
| 7 | DSM Delvotest ® MCS test with sucrose (plate) | 150 | 7.32 |

T = time required for a sample without antibiotic to induce a significant change in indicator status.

All commercially available test systems investigated (entries 1-5) showed pH values ranging from 6.79 to 7.16. The test systems of the present invention, with added sucrose (entries 6 and 7) showed pH values ranging from 7.32 to 7.47. The initial color of the indicator (in these cases purple) was more intense for entries 6-7 than for entries 1-5, which resulted in a more discrete and easier observation of the change of color (in these cases to yellow).

Example 3

Determination of Color Values of Several Commercially Available and Newly Developed Test Systems as a Function of Antibiotics Concentration Using the scanning technology outlined in the second aspect of the invention, the color values of various test systems as a function of various concentrations of penicillin G (0, 1, 2, 3, 4, 5 and 6 ppb) in milk was established using the composite function $Z=w_L \cdot L+w_a \cdot a+w_b \cdot b$. The results of these experiments are shown in FIG. 1. As can be seen from FIG. 1, the commercially available test systems from Copan and DSM (graphs marked Δ, ◇ and □) all displayed similar maximum Z-values around 13±2. In contrast, the test system of the present invention with sucrose added (graph marked ○) displayed a maximum Z-value of 22, which greatly facilitates accurate determination of the change in color. In addition, the higher Z-values and the steepness of the curve in FIG. 1 of the test system of the present invention also indicates an improved sensitivity, in this case towards penicillin G.

Example 4

Effect of Different Disaccharides as Nutrient Source in Test Systems

In order to establish the effect of reducing and non-reducing oligosaccharides, the following series of experiments was carried out. As a reference, a commercially available test system without any added oligosaccharide (DSM Delvotest® MCS test) was used. In addition, four different test systems were prepared by modifying the reference test by adding reducing lactose or non-reducing sucrose as outlined in the Table below. The difference in time required for a sample without antibiotic to induce a significant change in indicator of the different test systems compared to the reference test system was determined together with a visual determination of the test system towards two different antibiotics. To this end five different concentrations of penicillin G (1, 2, 3, 4 and 5 ppb) were measured and also five different concentrations of sulfadiazine (25, 50, 100, 150 and 250 ppb) were measured. Milk (100 µl) spiked with the mentioned concentrations of antibiotic was added at 64 C to test medium (250 µl). The tests were visually determined at the point in time were a sample without antibiotic had changed color.

| Supplement to reference test system (DSM Delvotest ® MCS) | T (min) | ΔT (min) | Detection limit penicillin G (ppb) | Detection limit sulfadiazine (ppb) |
|---|---|---|---|---|
| — | 145 | — | 2 | 50 |
| Sucrose (1.32 g · l$^{-1}$) | 135 | −10 | 2 | 50 |
| Lactose (0.66 g · l$^{-1}$) | 150 | 5 | 3 | 50 |
| Lactose (1.32 g · l$^{-1}$) | 155 | 10 | 3 | 50 |
| Lactose (2.64 g · l$^{-1}$) | 165 | 20 | 3 | 100 |

T = time required for a sample without antibiotic to induce a significant change in indicator status.
ΔT = difference in time compared to reference sample The results indicate that addition of non-reducing sucrose results in a test system having a shorter test duration compared with the reference test system (due to the improved readability at increased pH values). On the other hand, addition of reducing lactose results in a test system with an increased test duration and loss of sensitivity towards penicillin G and, to a lesser extent, sulfadiazine.

Example 5

Effect of Different Disaccharides as Nutrient Source in Test Systems

Example 4 was repeated with a double amount of microorganisms present in the test systems.

The results, summarized in the Table below, indicate that addition of non-reducing sucrose results in a test system having a test duration comparable with the reference test system but with improved sensitivity towards both penicillin G and sulfadiazine. On the other hand, addition of reducing lactose results in a test system with an increased test duration and loss of sensitivity towards sulfadiazine.

| Supplement to reference test system (DSM Delvotest ® MCS) | T (min) | ΔT (min) | Detection limit penicillin G (ppb) | Detection limit sulfadiazine (ppb) |
|---|---|---|---|---|
| — | 130 | — | 3 | 100 |
| Sucrose (1.32 g · l$^{-1}$) | 130 | 0 | 2 | 50 |
| Lactose (0.66 g · l$^{-1}$) | 140 | 10 | 3 | 100 |
| Lactose (1.32 g · l$^{-1}$) | 142 | 12 | 3 | 50 |
| Lactose (2.64 g · l$^{-1}$) | 156 | 26 | 3 | 100 |

T = time required for a sample without antibiotic to induce a significant change in indicator status.
ΔT = difference in time compared to reference sample

The invention claimed is:

1. A method for determining the presence or absence of an antibiotic in a fluid by a test system, which comprises a test medium comprising a thermophilic test organism, at least one substance that provides a solid substrate, nutrients, and an indicator; said method comprising:
   (a) contacting a sample of said fluid with said test medium,
   (b) incubating said test organism for a period of time to grow said test organism when no antibiotic is present in said sample, and
   (c) detecting growth or inhibition of growth of said test organism with said indicator;
   wherein said test medium further comprises sucrose in an amount of between 1.32 and 50 g/l to improve the sensitivity of said test system.

2. The method according to claim 1, wherein the amount of sucrose is between 2 and 50 g/l.

3. The method according to claim 1, wherein said thermophilic test organism is selected from the group consisting of *Bacillus* species and *Streptococcus* species.

4. The method according to claim 1, wherein said thermophilic test organism is *Bacillus stearothermophilus*.

5. The method according to claim 1, wherein said thermophilic test organism is *Streptococcus thermophilus*.

6. The method according to claim 1, wherein said thermophilic test organism is *Bacillus stearothermophilus* and *Streptococcus thermophilus*.

7. The method according to claim 1, wherein said at least one substance that provides a solid substrate is agar.

8. The method according to claim 1, wherein said at least one substance that provides a solid substrate is gelatin.

9. The method according to claim 1, wherein said at least one substance that provides a solid substrate is agar and gelatin.

10. The method according to claim 1, wherein said indicator is a pH-indicator.

11. The method according to claim 1, wherein said indicator is a redox-indicator.

12. The method according to claim 1, wherein said fluid in which antibiotics are to be determined is a fluid obtainable from an animal or human body.

13. The method according to claim 1, wherein said test medium further comprises a monosaccharide.

14. The method according to claim 13, wherein said monosaccharide is glucose.

* * * * *